United States Patent [19]

Grasselli et al.

[11] Patent Number: 5,349,117
[45] Date of Patent: Sep. 20, 1994

[54] PROCESS FOR SORPTION SEPARATION

[75] Inventors: Robert K. Grasselli, Chadds Ford; Rudolph M. Lago, Yardley; Richard F. Socha, Newtown, all of Pa.; John G. Tsikoyiannis, Princeton, N.J.

[73] Assignee: Mobil Oil Corp., Fairfax, Va.

[21] Appl. No.: 148,946

[22] Filed: Nov. 8, 1993

Related U.S. Application Data

[63] Continuation-in-part of Ser. No. 910,861, Jul. 8, 1992, Pat. No. 5,310,714.

[51] Int. Cl.$^5$ ................................................. C07C 7/13
[52] U.S. Cl. ........................... 585/820; 585/824; 208/310 Z; 502/407; 502/415
[58] Field of Search .......................... 585/820, 824; 208/310 Z; 502/407, 415

[56] References Cited

U.S. PATENT DOCUMENTS

| | | | |
|---|---|---|---|
| Re. 29,948 | 3/1979 | Dwyer et al. | 208/110 |
| 3,702,886 | 11/1972 | Argauer et al. | 423/328 |
| 3,709,979 | 1/1973 | Chu | 423/328 |
| 3,832,449 | 8/1974 | Rosinski et al. | 423/328 |
| 4,016,245 | 4/1977 | Plank et al. | 423/328 |
| 4,046,859 | 9/1977 | Plank et al. | 423/328 |
| 4,076,842 | 2/1978 | Plank et al. | 423/328 |
| 4,771,029 | 9/1988 | Pereira et al. | 502/355 |
| 4,800,187 | 1/1989 | Lachman et al. | 502/64 |
| 5,019,667 | 5/1991 | Chao et al. | 585/820 |
| 5,041,693 | 8/1991 | Zarchy | 208/310 Z |
| 5,220,099 | 6/1993 | Schreiner et al. | 208/3102 |
| 5,276,246 | 1/1994 | McCulloch et al. | 585/820 |

OTHER PUBLICATIONS

Lachman, I. M. et al., "Extruded Monolithic Catalyst Supports", American Chemical Society Meeting, 535–543 (Aug. 1991).

*Primary Examiner*—Anthony McFarlane
*Attorney, Agent, or Firm*—Alexander J. McKillop; Malcolm D. Keen; Dennis P. Santini

[57] ABSTRACT

A process for separating at least one component from a mixture of components which comprises contacting the mixture with a sorbent structure comprising a film of interconnected zeolite crystals bonded to a substrate, said sorbent structure being characterized by a value r representing the mg of zeolite/cm$^2$ of substrate surface and a value e representing the coating efficiency as mg of bonded zeolite/mg of YO$_2$ initially in the synthesis mixture, wherein r is at least 0.5 and e is at least 0.05.

19 Claims, 2 Drawing Sheets

5,349,117

PROCESS FOR SORPTION SEPARATION

CROSS-REFERENCE TO RELATED APPLICATIONS

This application is a continuation-in-part of application Ser. No. 07/910,861, now U.S. Pat. No. 5,310,714.

FIELD OF THE INVENTION

This invention relates to use of a novel structure composition in a process for separating at least one component from a mixture of components. The separation process comprises contacting the mixture with a structure comprising a zeolite film of continuously intergrown zeolite crystals strongly bonded to the surface of a substrate or monolith.

BACKGROUND OF THE INVENTION

Synthetic zeolites have been used as adsorptive separation agents for gases and liquids, and as catalysts. Generally, zeolites have been synthesized to yield a powder form of the crystalline material which can be formed or extruded into granules, beads or pellets, often incorporated with a binder such as clay or alumina.

Zeolites, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. The zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); ZK-5 (U.S. Pat. No. 3,247,195); ZK-4 (U.S. Pat. No. 3,314,752); ZSM-5 (U.S. Pat. No. 3,702,886); ZSM-11 (U.S. Pat. No. 3,709,979); ZSM-12 (U.S. Pat. No. 3,832,449); ZSM-20 (U.S. Pat. No. 3,972,983); ZSM-35 (U.S. Pat. No. 4,016,245); ZSM-38 (U.S. Pat. No. 4,046,859); and ZSM-23 (U.S. Pat. No. 4,076,842), merely to name a few.

The $SiO_2/AlO_2O_3$ mole ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S. Pat. No. 3,941,871 (Re. 29,948) discloses a porous crystalline silicate made from a reaction mixture containing no deliberately added aluminum in the synthesis mixture and exhibiting the X-ray diffraction pattern characteristics of ZSM-5. U.S. Pat. Nos. 4,061,724; 4,073,865; and 4,104,294 describe crystalline silicates or organosilicates of varying alumina and metal content.

Although zeolites include materials containing silicon and aluminum, it is recognized that the silicon and aluminum atoms may be replaced in whole or in part with other elements. More particularly, Ge is an art recognized substitute for Si. Also, B, Cr, Fe and Ga are art recognized replacements for Al. Accordingly, the term zeolite as used herein shall connote not only materials containing silicon and, optionally, aluminum atoms in the crystalline lattice structure thereof, but also materials which contain suitable replacement atoms for such silicon and/or aluminum.

Monolithic substrates such as wash coated ceramics, described, for example, in U.S. Pat. No. 4,771,029, and extruded catalytic monoliths, described, for example, by Lachman et al., in "Extruded Monolithic Catalyst Supports," *Symposium on Catalyst Supports: Chemistry, Forming and Characteristics*, American Chemical Society, New York City Meeting, 535–543 (1991), have been described as useful in emissions control.

U.S. Pat. No. 4,800,187 describes a method for crystallizing a zeolite on the surface of a ceramic monolith containing silica with a crystallization mixture containing a ratio of $H_2O/SiO_2$ of 16–20 to 1 and a ratio of $SiO_2/Al_2O_3$ of 1 to 0.0–0.4 for the synthesis of ZSM-5. Different ratios are described for large pore zeolites X and Y.

Now it has been found that the structure of a composition comprising a zeolite and substrate support improves the efficacy of certain sorption separation processes.

The structure composition for use herein and the method for its manufacture are novel and provide an improved sorption separation process.

SUMMARY OF THE INVENTION

This invention provides a process for use of a novel structure composition as a sorption separation media component. The structure composition for use herein comprises a film of interconnected zeolite crystals bonded to a substrate surface. The structure is characterized by a value r representing an amount of zeolite bonded to the substrate expressed as mg of zeolite/$cm^2$ of substrate surface, and r is at least about 0.5, preferably from about 1 to about 50.

In manufacturing the structure for use herein, a chemical mixture capable of forming the zeolite is prepared wherein the mixture comprises a $H_2O/YO_2$ molar ratio of at least about 25, Y comprising a tetravalent element, and a substrate is contacted with the mixture under crystallization conditions characterized by a value d wherein d = the ratio of $YO_2$ content of the chemical synthesis mixture to substrate superficial surface area in mg/$cm^2$; and d is at least about 0.5 and less than about 200; preferably from about 2 to about 50;

so that an essentially continuous layer of zeolite forms as bonded to the substrate. Y is preferably silicon, germanium or titanium.

The coating efficiency, e, expressed as mg of zeolite bonded to the substrate/mg of $YO_2$ initially present in the synthesis mixture may be calculated according to the formula: e=r/d. According to the method described, e is at least about 0.05, preferably at least about 0.1 and can reach values close to 1.

Advantageously, in the structure for use herein the zeolite film is strongly bonded to the surface of the substrate so that the mechanical integrity of the film is maintained when the structure is exposed to high flow rates of gases or liquids.

An embodiment of the present process provides for sorption of at least one component from a mixture of components having different sorption characteristics with respect to the structure described above. The mixture is contacted with a catalytically inactive form of the structure to selectively sorb at least one component of the mixture.

Another embodiment of the present process provides for sorption and retention of hydrocarbons contained in exhaust gases. This process embodiment involves contacting the gas with the structure at low temperature, such as during the startup period of an internal combustion engine, and removing the hydrocarbons from the exhaust gas prior to releasing same to the atmosphere.

DESCRIPTION OF THE PREFERRED EMBODIMENTS

The entire contents of application Ser. No. 07/910,861 are incorporated herein by reference as to description of the sorption media structure composition for use herein and its manufacture.

In the manufacture of the structure for use herein, a zeolite film is synthesized as bonded to a substrate. "Bonded" is intended to mean that the film is strongly adherent to the surface of a substrate and remains substantially adherent when subjected to conditions of catalysis, particularly high flow-through of gases and liquids. The film consists of an array of substantially continuously intergrown crystals which are connected to each other. This intergrowth is important for the mechanical integrity of the film.

In order to synthesize the film for the structure used in the invention, the composition of the crystallization reaction mixture has a minimum $H_2O/YO_2$ molar ratio, as calculated by conventional methods, which increases as the reaction mixture $YO_2/X_2O_3$ molar ratio decreases, Y being a tetravalent element, preferably silicon, germanium or titanium, and X being a trivalent element, preferably aluminum, iron, boron or gallium.

Figure 1:
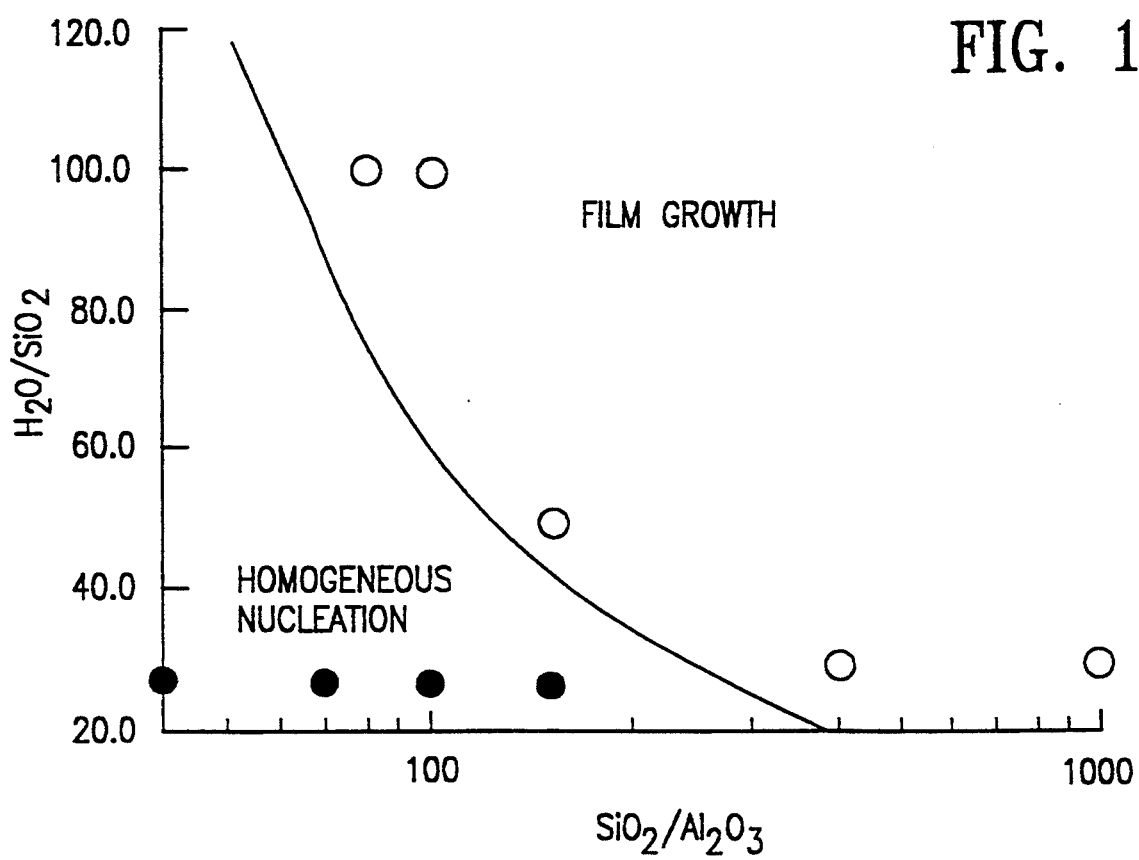
FIG. 1 is a graph demonstrating molar ratios of synthesis components for film growth.

For example, as shown in FIG. 1, in the reaction mixture, if

| $SiO_2/Al_2O_3$ | and | $H_2O/SiO_2$ |
| --- | --- | --- |
| 1000 | | 28 |
| 400 | | 30 |
| 150 | | 50 |
| 80 | | 100 | then crystallization occurs substantially on the substrate surface and homogeneous nucleation is minimized.

However, if

| $SiO_2/Al_2O_3$ | and | $H_2O/SiO_2$ |
| --- | --- | --- |
| 150 | | 28 |
| 100 | | 28 |
| 80 | | 28 |
| 50 | | 28 | then substantial homogeneous nucleation occurs leading to powder precipitation to the bottom of the crystallization vessel with very little zeolite adhering on the substrate.

For maximum coating efficiency, when the $YO_2/X_2O_3$ ratio in the reaction mixture is greater than about 400, the $H_2O/YO_2$ in the reaction mixture is at least about 25. When the $YO_2/X_2O_3$ is greater than about 150 and less than about 400, the $H_2O/YO_2$ is at least about 35. When the $YO_2/X_2O_3$ is less than about 150, the $H_2O/YO_2$ is at least about 45.

Accordingly, the crystallization mixture has a composition in terms of mole ratios including:

| $H_2O/YO_2$ | 25 to 500 |
| --- | --- |
| $YO_2/X_2O_3$ | 26 to ∞ |
| $OH^-/YO_2$ | 0.01 to 0.8 | wherein X is a trivalent element and Y is a tetravalent element.

A preferred crystallization mixture includes:

| $H_2O/YO_2$ | 30 to 200 |
| --- | --- |
| $YO_2/X_2O_3$ | 40 to ∞ |
| $OH^-/YO_2$ | 0.02 to 0.4 |

A more preferred crystallization mixture includes:

| $H_2O/YO_2$ | 30 to 150 |
| --- | --- |
| $YO_2/X_2O_3$ | 50 to ∞ |
| $OH^-/YO_2$ | 0.02 to 0.4 |

Typical zeolites to be synthesized according to this method are characterized by a Constraint Index of about 1 to about 12. The Constraint Index is a convenient measure of the extent to which a zeolite provides constrained access to molecules of varying sizes to its internal structure. The method by which Constraint Index is determined is described fully in U.S. Pat. No. 4,016,218, incorporated herein by reference for details of the method.

Zeolites which conform to the specified values of Constraint Index for medium pore zeolites include, for example, ZSM-5, ZSM-11, ZSM-12, ZSM-22, ZSM-23, ZSM-35, ZSM-38, ZSM-5/ZSM-11 intermediate, and ZSM-48, i.e., particularly zeolites which are described, for example, in U.S. Pat. Nos. 3,702,886 and Re. No. 29,948; 3,709,979; 3,832,449; 4,556,477; 4,076,842; 4,016,245; 4,046,859; 4,229,424; and 4,397,827 to which reference is made for details of these zeolites. These zeolites may be produced with differing silica:alumina ratios ranging from 12:1 upwards. They may, in fact, be produced from reaction mixtures from which aluminum is intentionally excluded, so as to produce materials having extremely high silica:alumina ratios which, in theory at least may extend up to infinity. Silica:alumina ratios of at least 30:1 and higher will be common for these zeolites, e.g., 70:1, 200:1, 500:1, 1600:1 or even higher. Highly siliceous forms of zeolites ZSM-5, ZSM-11 and ZSM-12 are described, respectively, in U.S. Pat. No. Re. 29,948 and European Patent Publication No. 14,059 to which reference is made for details of these zeolites. Also included herein is Zeolite Beta which has a Constraint Index in the range of approximately 0.6–2.0, and which is described in U.S. Pat. No. 3,308,069 and Re. No. 28,341.

Structure Manufacture

A reaction mixture is prepared preferably containing an oxide of Y, preferably silicon, optionally a source of X, preferably aluminum, a templating agent which is an organic nitrogen containing compound, and an alkaline aqueous medium.

The sources of alkali metal oxide may be, for example, sodium, lithium, calcium, magnesium, cesium or potassium hydroxides, halides (e.g., chlorides, and bromides), sulfates, nitrates, acetates, silicates, aluminates, phosphates and salts of carboxylic acids.

The Y, e.g., silicon, oxide can be supplied from known sources such as silicates, silica hydrosol, precipitated silica hydrosol, precipitated silica, e.g., Hi-Sil, silica gel, silica acid. The X, e.g., aluminum, oxide, may be provided as only an impurity in another reactant, e.g., the Y, e.g., silica, source.

The sources of organic nitrogen-containing cations, depending, of course, on the particular zeolite product to result from crystallization from the reaction mixture, may be primary, secondary or tertiary amines or quaternary ammonium compounds. Non-limiting examples of quaternary ammonium compounds include salts of tetramethylammonium, tetraethylammonium, tetrapropylammonium, tetrabutylammonium, diethylammonium, triethylammonium, dibenzylammonium, dibenzyldimethylammonium, dibenzyldiethylammonium, benzyltrimethylammonium and chlorine. Non-limiting examples of amines useful herein include the compounds of trimethylamine, triethylamine, tripropylamine, ethylenedimine, propanediamine, butanediamine, pentanediamine, hexanediamine, methylamine, ethylamine, propylamine, butylamine, diamethylamine, diethylamine, dipropylamine, benzylamine, aniline, pyridine, piperidine and pyrrolidine.

In forming the films, a substrate is contacted with a chemical reaction mixture as described above capable of forming the desired zeolite and under crystallization conditions. After a period of time under suitable conditions, a cohesive film is formed adherent to the surface of the substrate. The orientation of the substrate surface in the reaction mixture is not critical, but it is preferably fully immersed in the synthesis solution, for a time greater than about 2 hours to about 1,000 hours, preferably at least about 4.5 hours, more preferably from about 12 hours to about 120 hours; at a temperature of from about 50° C. to about 230° C., preferably from 100° C. to about 220° C.; and at a pressure from about 1 atmosphere to about 100 atmospheres, preferably from about 1 atmosphere to about 15 atmospheres.

The films are produced by synthesis under hydrothermal conditions on the substrate. Substrates contemplated to be used herein include, as non-limiting examples, metals such as Fe, Co, Ni, Sn, Ag, Pd, Pt, Cu and stainless steel, particular metals being Fe, Al, Cu, Ni and stainless steel; ceramics such as glass, clays (e.g., kaolinites, montmorillonites, and illites), quartz, mullite, titania, cordierite, zirconia, silica, alumina, spinel, carbides and nitrides (such as those of silicon, boron, zirconium, hafnium, tantalum, vanadium, molybdenum, tungsten and niobium). It is not necessary that the substrate contain silicon or aluminum.

The substrate may be an extruded monolith. Extruded monoliths of low surface area such as cordierite which may be in honeycomb shape, are advantageously used in emissions control from internal combustion engines. Other extruded monoliths of higher surface area such as titania, alumina, silica, zirconia and extruded zeolites are advantageously used in $NO_x$ emissions control such as in Selective Catalytic Reduction (SCR). Monoliths may also incorporate in their compositions, various inorganic additives such as glass particles, metal particles or diatomaceous earth.

The substrates may have various configurations. For example, the surface may be flat, curved, honeycomb shaped, layered plate form, etc.

The synthesis conditions for crystallization of a zeolite as adherent to a substrate may be further defined by a value d which is the ratio of the $YO_2$ or silica content of the synthesis hydrogel to the superficial surface area of the substrate ($mg/cm^2$). The product zeolite film-coated substrate may be characterized by the zeolite loading, i.e., the amount of zeolite adhering to the surface, a value r (mg of zeolite/$cm^2$), and by the coating efficiency e, i.e., the ratio of the amount of zeolite adhering to the substrate to the amount of silica initially present in the crystallization mixture, wherein $e = r/d$ For maximum coating efficiency, d is less than 200, preferably from about 0.5 to about 200, more preferably in the range of from about 2 to about 50; r is at least about 0.5, preferably from about 1 to about 50; and e is at least about 0.05 preferably from about 0.1 to about 1.0.

The zeolite coated substrates can be modified for a particular use by post synthesis treatment using well known techniques, in order to alter their catalytic and/or adsorption properties as desired for a particular application. For example, the structure can be steamed at a temperature of about 200° C. to 800° C. for about 1 to 50 hours. The structure can also be calcined.

Zeolites can be used either in the alkali metal form, e.g., the sodium or potassium form; the ammonium form; the hydrogen form or another univalent or multivalent cation form. For use in this process, the catalyst structure comprising the zeolite will be subjected to thermal treatment to remove part or all of the zeolite organic constituent. Aluminum may be incorporated into the zeolite framework by treatment with aluminum halide.

The original alkali metal cations of the as synthesized zeolite can be replaced in accordance with techniques well known in the art, at least in part, by ion exchange with other cations. Preferred replacing cations include metal ions, hydrogen ions, hydrogen precursor, e.g., ammonium ions, and mixtures thereof. Replacing cations may include hydrogen, rare earth metals and metals of Groups 3–12 of the Periodic Table of the Elements (New Notation. See, e.g., *CRC Handbook of Chemistry and Physics,* 69th ed. (1988)).

A typical ion exchange technique would be to contact the synthetic zeolite with a salt of the desired replacing cation or cations. Examples of such salts includes the halides, e.g., chlorides, nitrates and sulfates.

The zeolite films described herein can be used in intimate combination with an oxidation-reduction component such as tungsten, vanadium, molybdenum, rhenium, copper, nickel, cobalt, chromium, manganese, or a noble metal such as platinum or palladium where a hydrogenation-dehydrogenation function is performed. Such component can be exchanged into the composition to the extent atom X, e.g., aluminum, is in the structure, impregnated in or on to it such as for example, by, in the case of platinum, treating the coated molecular sieve having ion exchange capacity with a solution containing a platinum metal-containing ion. Thus, suitable platinum compounds include chloroplatinic acid, platinum chloride, and various compounds containing the platinum amine complex.

The metal containing zeolite film structures may have essentially no acid activity, or they may have substantial acid activity to provide for dual functional catalysis. The catalytic activity of the structures can be adjusted from essentially zero to high activity, depending on the particular use thereof.

The zeolite film coated substrates for use in the present invention should usually be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing the bonded molecular sieve in a vacuum, but a longer time is required to obtain a sufficient amount of dehydration.

The zeolite coated substrate has sorption affinity for hydrocarbons and utility for removing atmospheric pollutants from industrial exhaust gases.

The term industrial exhaust gas as used herein means any waste gas which is formed in an industrial process or operation and which is normally disposed of by discharge to the atmosphere. The composition of such a gas varies and depends on the particular process or operation which leads to its formation. When formed in the combustion of fossil fuels, it will generally contain oxygen, nitrogen, steam, carbon dioxide, carbon monoxide, unburned hydrocarbons especially olefins and aromatics resulting from incomplete combustion, and $NO_x$ at relatively low levels, such as up to about 1,000 ppm of nitric oxide plus nitrogen dioxide. Sulfur-containing fuels will produce an exhaust gas that contains some $SO_x$ including sulfur dioxide and sulfur trioxide.

Industrial exhaust gases include flue gases produced, for example, by incinerators, turbines, $HNO_3$ plants, coal-fired and fossil-fueled power plants, and internal combustion engines. Methods of removal of the pollutants include catalytic oxidation, e.g., of unburned hydrocarbons and carbon monoxide, reduction of $NO_x$ and adsorption or absorption of hydrocarbons and $SO_x$.

Examples of particular applications of the structure for use herein include removal of unburned hydrocarbons such as $C_3$–$C_6$ paraffins and olefins, and aromatics, from cold engine flue gas using the hydrogen or alkali metal ion exchanged structure, which may be impregnated with oxidation metal components including, for example, Pt, Cu, Ni and V.

The films can also be used as adsorbents and separation vehicles in fine chemical applications. At least one component in a mixture of components can be partially or substantially separated from a mixture of components having differential sorption characteristics with respect to the zeolite film by contacting the mixture with the film to selectively sorb the one component. Examples of this include contacting a mixture comprising water and at least one hydrocarbon component, whereby at least one hydrocarbon component is selectively sorbed. Another example includes sorption of at least one hydrocarbon component from a mixture comprising same and at least one additional hydrocarbon component.

In order to more fully illustrate the nature of the invention and the manner of practicing same, the following examples are presented.

EXAMPLES 1–18

The following substrates were prepared:
(a) Pyrex glass plate (Corning Glass Works, Corning, N.Y.) 4 cm×3 cm×0.4 cm
(b) Cordierite Monolith (Corning Glass Works, Corning, N.Y.) cylindrical, diameter=one inch height-=one inch, 100 cells/sq. inch
(c) Cordierite Monolith (Corning Glass Works, Corning, N.Y.) cylindrical, diameter=one inch height-=one inch, 400 cells/sq.inch
(d) Mullite Monolith (Corning Glass Works, Corning, N.Y.) cylindrical, diameter=one inch height=one inch, 100 cells/sq. inch From the geometry of the monolith substrates, the surface area available for coating with zeolite was estimated to be about 170 $cm^2$ for substrates b and d and about 360 $cm^2$ for substrate c.

A synthesis hydrogel was prepared consisting of varying amounts of distilled water, NaOH, tetrapropylammonium bromide (TPABr) colloidal silica (Ludox AS-40) and $NaAlO_2$. First a solution was prepared by dissolving varying quantities of NaOH, TPABr and $NaAlO_2$ in distilled water under stirring. The colloidal silica sol was added to the basic solution and the final hydrogel stirred to produce a homogeneous solution. The substrates a, b, c, d were separately calcined in air, cooled, weighed and suspended vertically in the center of 125 ml tetrafluoroethylene (Teflon) non-stirred autoclaves so that the external surfaces of the substrates were oriented vertically. The vertical orientation was chosen to minimize gravitational deposition of homogeneously nucleated crystals (i.e., crystals not bonded to the substrate). The substrate was also not in contact with the bottom of the autoclave. The prepared synthesis hydrogel was poured into the vessel until the substrate was fully immersed, the autoclave sealed and placed inside a preheated convection oven. The autoclave was removed from the oven after a specified time period, the substrate removed from the solution, washed under flowing distilled water, dried, calcined and weighed. The weight of each substrate was higher than its weight before synthesis due to film deposition. The presence of a ZSM-5 film was confirmed by x-ray diffraction and Scanning Electron Microscopy (SEM). The results are summarized in Table I below.

In the Table, the composition of the synthesis hydrogel is defined by
$SiO_2/Al_2O_3$
$H_2O/SiO_2$
$OH^-/SiO_2$
$TPABr/SiO_2$ The synthesis conditions are defined by synthesis temperature, T (° C.); crystallization time, t (days); and the ratio of the silica content of the synthesis hydrogel to the substrate superficial surface area, d (mg/cm$^2$).

The coated substrate is characterized by zeolite loading, r (mg of zeolite/cm$^2$); and coating efficiency, e (mg of zeolite on substrate/mg of silica initially present in solution), where $$e = r/d$$

Figure 2:
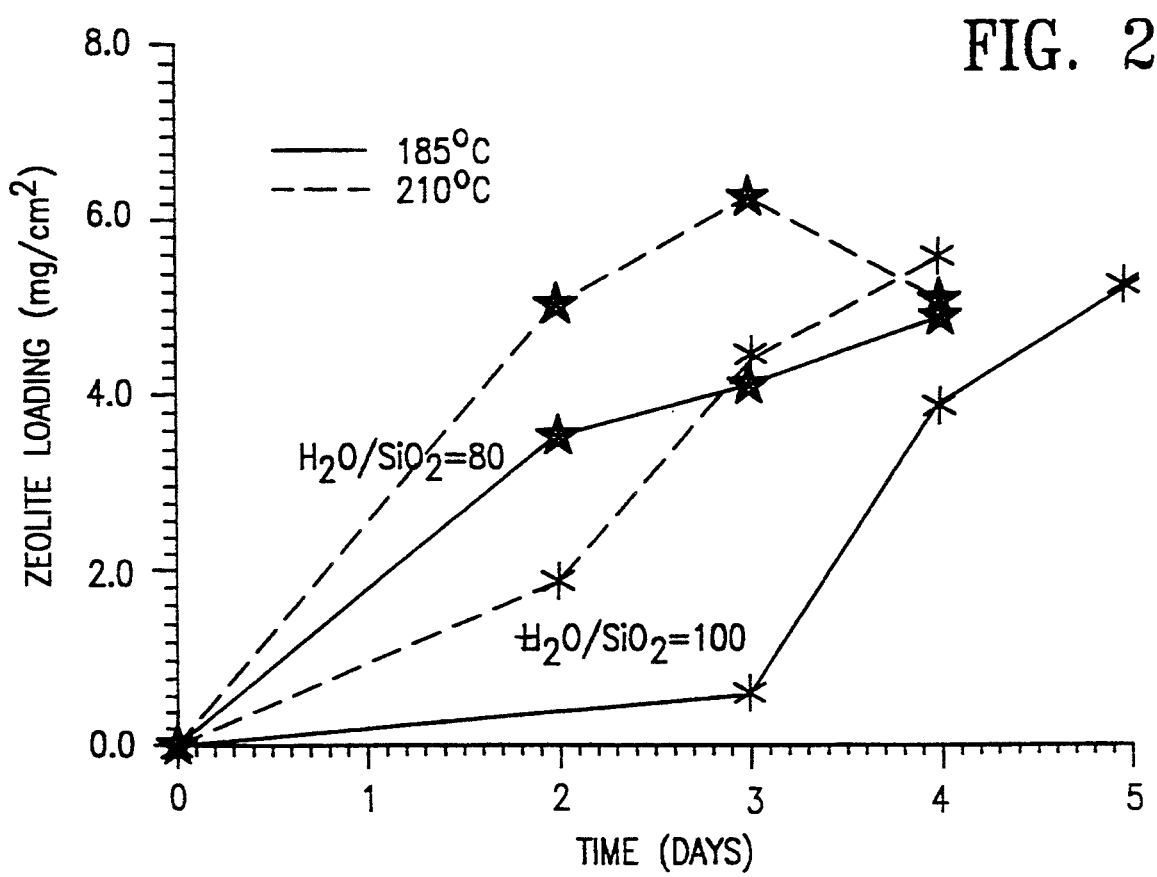
FIG. 2 is a graph representing zeolite loading on monoliths after various times at two temperatures and two $H_2O/SiO_2$ values.
Figure 3:
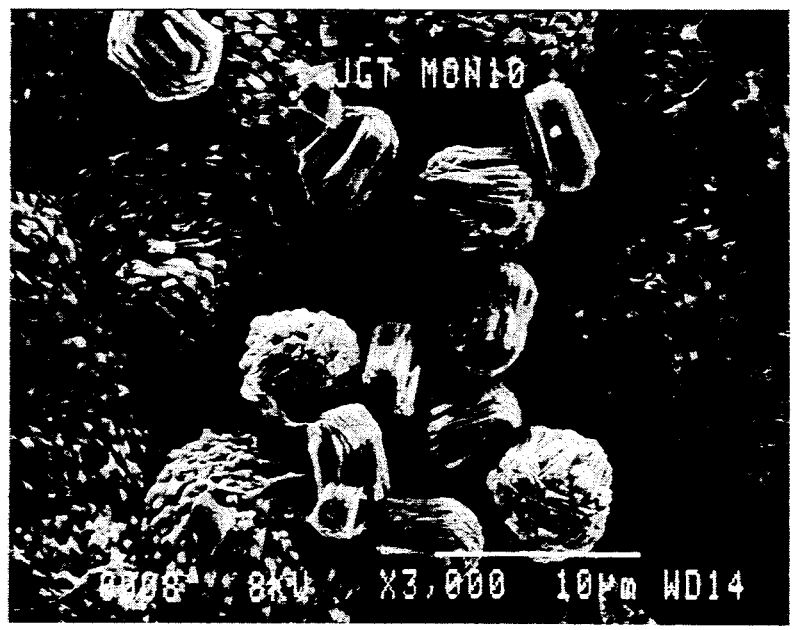
FIG. 3 is a Scanning Electronic Microscope (SEM) photomicrograph of the surface morphology of the bonded zeolite of Example 11 at 3,000 magnification.
Figure 4:
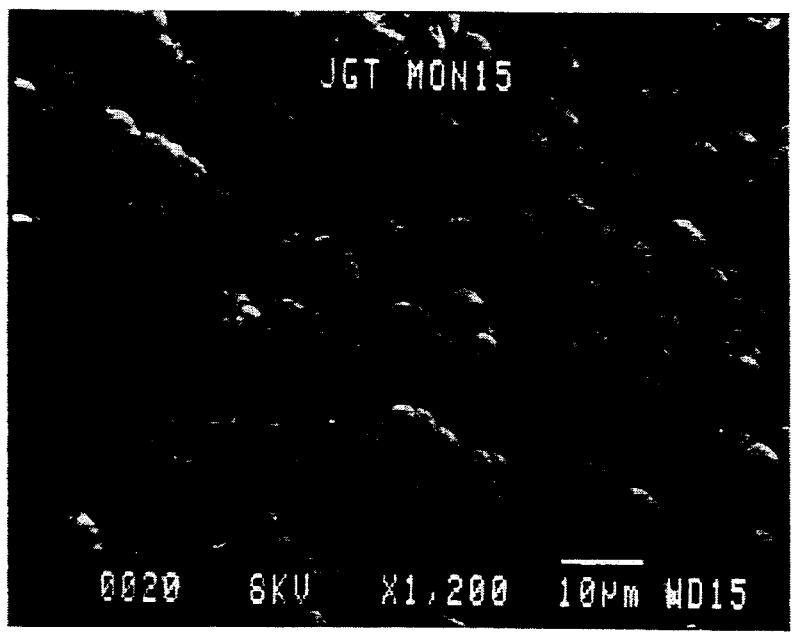
FIG. 4 is an SEM photomicrograph of the surface morphology of the bonded zeolite of Example 16 at 1,200 magnification.

The process conditions and results are summarized in Table I. Selected synthesis conditions are graphed in FIGS. 1 and 2. SEM of the films of Examples 11 and 16 is shown in FIGS. 3 and 4 respectively.

TABLE I

| Ex | $\frac{SiO_2}{Al_2O_3}$ | $\frac{H_2O}{SiO_2}$ | $\frac{OH^-}{SiO_2}$ | $\frac{TPABr}{SiO_2}$ | Subst. | T | t | d | r | e |
|---|---|---|---|---|---|---|---|---|---|---|
| 1 | ∞ | 30.0 | 0.025 | 0.055 | (a) | 180 | 3.0 | 460.0 | 46.0 | 0.10 |
| 2 | 80 | 100.0 | 0.10 | 0.10 | (a) | 180 | 5.0 | 63.0 | 15.1 | 0.24 |
| 3 | 80 | 30.0 | 0.025 | 0.055 | (a) | 180 | 3.0 | 460.0 | 0.0 | 0.00 |
| 4 | ∞ | 30.0 | 0.025 | 0.055 | (c) | 180 | 3.0 | 31.0 | 24.2 | 0.78 |
| 5 | ∞ | 30.0 | 0.025 | 0.055 | (b) | 180 | 1.0 | 18.0 | 11.5 | 0.64 |
| 6 | 400 | 30.0 | 0.025 | 0.055 | (c) | 180 | 3.0 | 31.0 | 19.5 | 0.63 |
| 7 | 150 | 50.0 | 0.065 | 0.075 | (b) | 180 | 5.0 | 32.0 | 9.6 | 0.30 |
| 8 | 100 | 100.0 | 0.10 | 0.10 | (c) | 180 | 8.0 | 8.5 | 6.55 | 0.77 |
| 9 | 100 | 100.0 | 0.10 | 0.10 | (c) | 180 | 5.0 | 50.0 | 11.0 | 0.22 |
| 10 | 100 | 100.0 | 0.10 | 0.10 | (b) | 180 | 5.0 | 95.0 | 6.65 | 0.07 |
| 11 | 100 | 100.0 | 0.10 | 0.10 | (b) | 180 | 9.0 | 16.0 | 7.36 | 0.46 |
| 12 | 100 | 100.0 | 0.10 | 0.10 | (d) | 180 | 9.0 | 16.0 | 8.64 | 0.54 |
| 13 | 80 | 100.0 | 0.10 | 0.10 | (b) | 180 | 1.7 | 16.0 | 0.48 | 0.03 |
| 14 | 80 | 100.0 | 0.10 | 0.10 | (b) | 180 | 3.0 | 16.0 | 1.12 | 0.07 |
| 15 | 80 | 100.0 | 0.10 | 0.10 | (b) | 180 | 4.0 | 16.0 | 1.60 | 0.10 |
| 16 | 80 | 100.0 | 0.10 | 0.10 | (b) | 180 | 5.0 | 16.0 | 6.40 | 0.40 |
| 17 | 80 | 100.0 | 0.10 | 0.10 | (d) | 180 | 5.0 | 16.0 | 5.76 | 0.36 |
| 18 | 80 | 20.0 | 0.10 | 0.10 | (b) | 180 | 5.0 | 40.0 | 1.20 | 0.03 |

All substrates, except in examples 3 and 18, were coated with a uniform layer of ZSM-5 which constituted from 2.4 to 179% of the substrate weight. Except for examples 3 and 18, solid particles in powder form were not observed, but only zeolite films coated the substrate and internal vessel walls were observed.

Under the conditions required here for structure composition manufacture, the weight of the zeolite film is maximized and the crystallization of homogeneously nucleated crystals is minimized. When the H$_2$O/SiO$_2$ ratio was outside the required parameters as shown in comparative example 18, homogeneously nucleated crystals which were not adherent to the substrate were formed. Furthermore, in Example 18, the zeolite loading of the monolith (r=1.2 mg/cm$^2$) and the coating efficiency (e=0.03) were much lower than the zeolite loading and coating efficiency attained under the synthesis conditions of the invention.

In general, the coating efficiency is less than 1.0 because at the end of the crystallization period, some silica may have remained in solution, coated the internal walls of the vessel or have formed homogeneously nucleated crystals which settled at the bottom of the synthetic vessel. This homogeneous nucleation is minimized under the conditions required herein.

EXAMPLE 19

Adsorption of Hydrocarbons from Exhaust Flue Gas

The cylindrical monolith of example 4 is inserted into a quartz reactor tube having an inside diameter of 1 inch. The monolith is calcined in air at 540° C. for four hours and cooled to 90° C. in nitrogen. A gas stream containing 1,500 ppm propylene in nitrogen is blown through the channels of the monolith at 400 cc/minute for 30 minutes. The effluent gas stream is collected and analyzed for hydrocarbon content, which proves to be 150 ppm propylene, i.e., smaller than the inlet concentration, due to adsorption and retention of propylene by the product structure of example 4.

EXAMPLE 20

Removal of p-Xylene Impurity from m-Xylene

The cylindrical monolith of example 4 is calcined in air at 540° C. for four hours and cooled to room temperature in dry helium. It is then contacted for 10 minutes with 10 g of m-xylene which contains 1 wt. % p-xylene as an impurity. After contact, the p-xylene impurity content of the liquid proves to be only 0.2 wt. % due to selective adsorption of p-xylene by the product structure of example 4.

What is claimed is:

1. A process for separating at least one component from a mixture of components in the vapor or liquid phase having differential sorption characteristics with respect to a sorbent structure, wherein said at least one component is selectively adsorbed on said sorbent in preference to at least one other component in said mixture of components said sorbent structure comprising a film of interconnected zeolite crystals bonded to a substrate surface, said structure having been manufactured by the method comprising contacting the substrate with a chemical reaction mixture capable of forming the zeolite film under crystallization conditions, wherein said reaction mixture comprises a H$_2$O/YO$_2$ molar ratio of at least about 25 when the YO$_2$/X$_2$O$_3$ molar ratio is greater than about 400, a H$_2$O/YO$_2$ ratio of at least about 35 when the YO$_2$/X$_2$O$_3$ ratio is greater than about 150 and less than about 400, and a H$_2$O/YO$_2$ ratio of at least about 45 when the XO$_2$/X$_2$O$_3$ ratio is less than about 150; and wherein Y is a tetravalent element and X is a trivalent element.

2. The process of claim 1 wherein said zeolite crystals have a Constraint Index of from about 1 to about 12.

3. The process of claim 1 wherein said zeolite crystals have the crystal structure of ZSM-5, ZSM-5/ZSM-11 intermediate, ZSM-11, ZSM-12, ZSM-22, ZSM-23, ZSM-35, ZSM-38, ZSM-48, or Beta.

4. The process of claim 1 wherein said zeolite crystals have the structure of ZSM-5.

5. The process of claim 1 wherein said substrate is selected from the group consisting of glass, cordierite, mullite, titania, zirconia, silica, carbides, nitrides, quartz, clay, and metals.

6. The process of claim 1 wherein said sorbent structure manufacturing method comprises steaming the zeolite at a temperature of from about 200° C. to about 800° C. for a time of from about 1 hour to about 50 hours.

7. The process of claim 1 wherein said sorbent structure manufacturing method comprises calcining the zeolite.

8. The process of claim 1 wherein said sorbent structure manufacturing method comprises ion exchanging the zeolite.

9. The process of claim 8 wherein said ion is selected from the group consisting of Pd, Pt, Ru, Mo, W, Ni, Cu, Fe, Ag, Co, Rh, V, Cr, and ammonium.

10. The process of claim 1 wherein the chemical reaction mixture has a composition in terms of mole ratios including

| | |
|---|---|
| $H_2O/YO_2$ | 25 to 500 |
| $YO_2/X_2O_3$ | 26 to $\infty$ |
| $OH^-/YO_2$ | 0.01 to 0.8. |

11. The process of claim 10 wherein the chemical mixture has a composition including

| | |
|---|---|
| $H_2O/YO_2$ | 30 to 200 |
| $YO_2/X_2O_3$ | 40 to $\infty$ |
| $OH^-/YO_2$ | 0.02 to 0.4. |

12. The process of claim 11 wherein the chemical mixture has a composition including

| | |
|---|---|
| $H_2O/YO_2$ | 30 to 150 |
| $YO_2/X_2O_3$ | 50 to $\infty$ |
| $OH^-/YO_2$ | 0.02 to 0.4. |

13. The process of claim 10 wherein X comprises at least one member selected from the group consisting of aluminum, boron, iron, and gallium; and Y comprises at least one member selected from the group consisting of silicon, germanium, and titanium.

14. The process of claim 13 wherein X comprises aluminum and Y comprises silicon.

15. The process of claim 1 wherein the chemical reaction mixture molar ratio of $YO_2$ to available surface area of the substrate in $mg/cm^2$ is a value d which is at least about 0.5 and less than about 200.

16. The process of claim 15 wherein d is from about 2 to about 50.

17. The process of claim 1 in which the mixture comprises water and at least one hydrocarbon component, at least one hydrocarbon component of the mixture being selectively sorbed on said sorbent in preference to the water in the mixture.

18. The process of claim 1 in which the mixture comprises at least two hydrocarbon component, at least one of which is selectively sorbed on said sorbent in preference to at least one other hydrocarbon component of the mixture.

19. The process of claim 1 in which the mixture comprises an alcohol and at least one hydrocarbon component, at least one hydrocarbon component of the mixture being selectively sorbed on said sorbent in preference to the alcohol in the mixture.

* * * * *